United States Patent
Fischer et al.

(10) Patent No.: US 7,965,815 B2
(45) Date of Patent: Jun. 21, 2011

(54) DEVICE AND METHOD FOR PROCESSING AND PRESENTATION OF X-RAY IMAGES

(75) Inventors: Daniel Fischer, Erlangen (DE); Rainer Graumann, Hochstadt (DE)

(73) Assignee: Siemens Aktiengesellschaft, Munich (DE)

( * ) Notice: Subject to any disclaimer, the term of this patent is extended or adjusted under 35 U.S.C. 154(b) by 203 days.

(21) Appl. No.: 12/252,510

(22) Filed: Oct. 16, 2008

(65) Prior Publication Data

US 2009/0097615 A1  Apr. 16, 2009

(30) Foreign Application Priority Data

Oct. 16, 2007 (DE) .......................... 10 2007 049 539

(51) Int. Cl.
 *G01N 23/04* (2006.01)
(52) U.S. Cl. .............................. 378/63; 378/37; 378/206
(58) Field of Classification Search .................... 378/63, 378/206
See application file for complete search history.

(56) References Cited

U.S. PATENT DOCUMENTS

| | | | | |
|---|---|---|---|---|
| 5,396,604 A * | 3/1995 | DeLano et al. | ................ | 712/207 |
| 5,539,798 A * | 7/1996 | Asahina et al. | ............... | 378/98.5 |
| 5,872,828 A * | 2/1999 | Niklason et al. | ................ | 378/23 |
| 6,305,842 B1 * | 10/2001 | Kunert | ........................... | 378/206 |
| 6,473,489 B2 | 10/2002 | Bani-Hashemi et al. | | |
| 7,198,404 B2 * | 4/2007 | Navab et al. | .................. | 378/206 |

FOREIGN PATENT DOCUMENTS

WO    WO 2005036148 A1 *    4/2005

\* cited by examiner

*Primary Examiner* — Hoon Song
*Assistant Examiner* — Mona M Sanei
(74) *Attorney, Agent, or Firm* — Schiff Hardin LLP

(57) ABSTRACT

In a device and method for processing and presenting x-ray images, an x-ray image of a subject is acquired with an x-ray acquisition cone simultaneously with the acquisition of an optical exposure of the examination subject with an optical acquisition cone that is congruent with the x-ray acquisition cone. The subject in the optical exposure is subjected to segmentation and/or edge extraction, and the extracted optical exposure and the x-ray image are additively combined so that the subject edges from the optical exposure are inserted into the x-ray image.

6 Claims, 2 Drawing Sheets

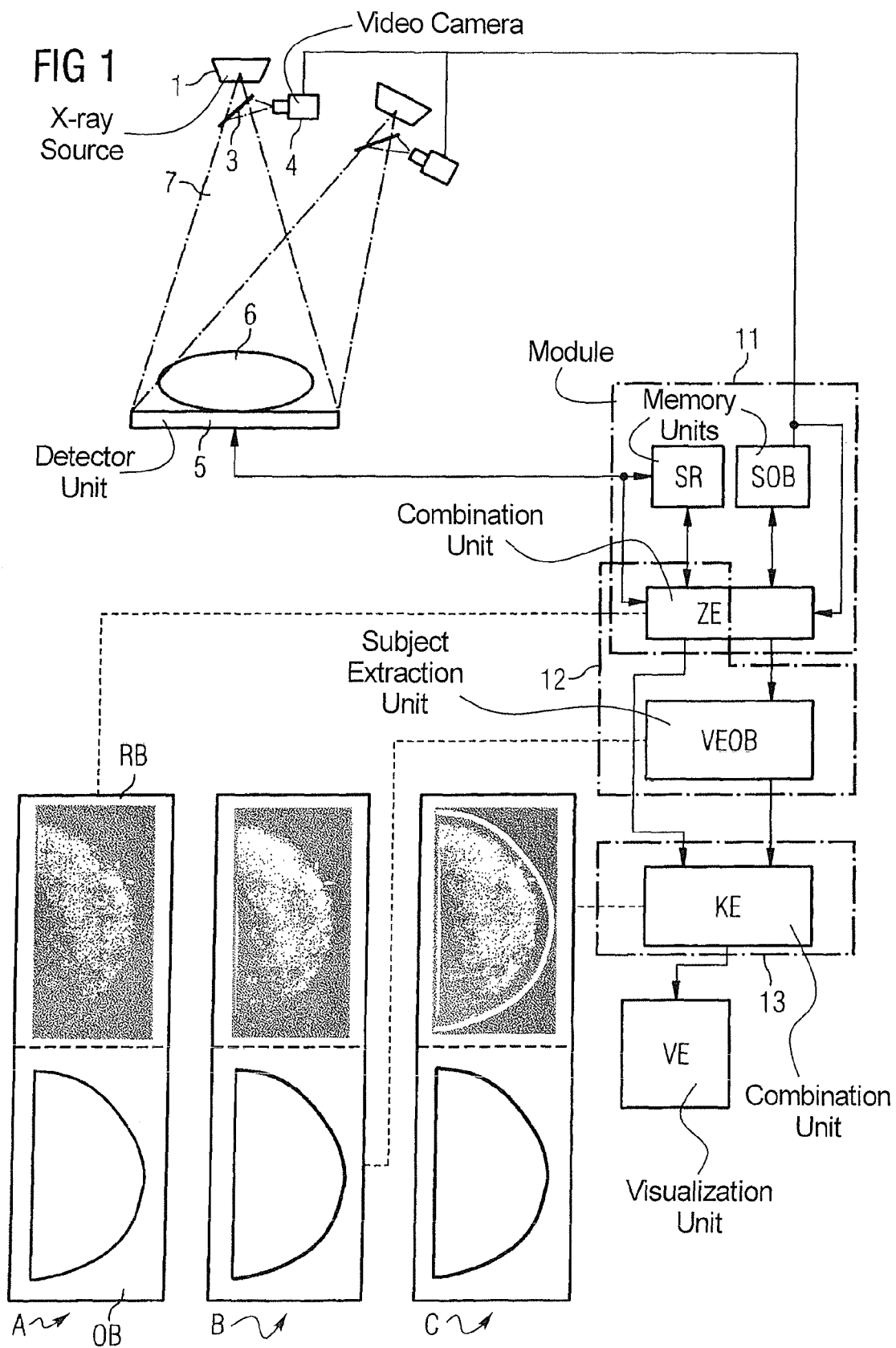

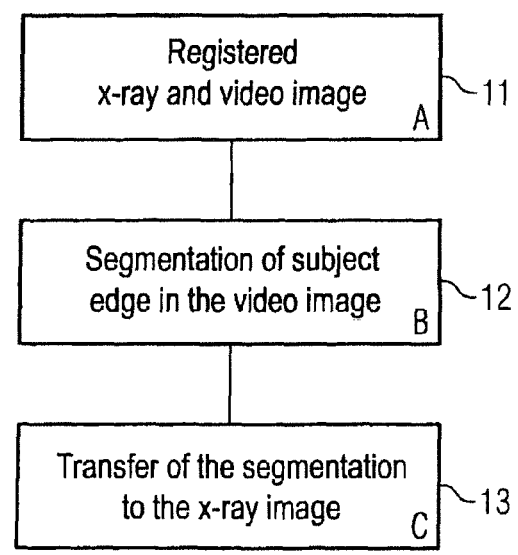

DEVICE AND METHOD FOR PROCESSING AND PRESENTATION OF X-RAY IMAGES

BACKGROUND OF THE INVENTION

1. Field of the Invention

The present invention concerns a device and a method for processing and presentation of x-ray images.

2. Description of the Prior Art

For diagnostic and therapeutic purposes it is helpful to isolate regions in x-ray images. A segmentation or subject recognition in x-ray images is implemented with segmentation or subject recognition algorithms, wherein the x-ray images used for this have been generated with a conventional x-ray dose. X-ray images that have been created with distinctly reduced individual image dose during a tomographic method (for example tomosynthesis) require a highly complex and time-consuming computation effort in order to implement a segmentation or a subject recognition with the segmentation or a subject recognition algorithms cited above since—due to the very low individual x-ray image dose—the x-ray images do not exhibit the contrast of the aforementioned x-ray images.

SUMMARY OF THE INVENTION

An object of the present invention is to provide an improved device and method for processing and presentation of subjects in x-ray images.

This object is achieved in accordance with the invention by a device for processing and presentation of x-ray images that has an x-ray acquisition unit as well as an optical acquisition unit, with the acquisition cones of the x-ray image of the x-ray acquisition unit as well as of the optical image of the optical acquisition unit being congruent, and wherein an x-ray acquisition and optical acquisition are triggered to occur at the same point in time, and having a subject extraction unit for segmentation and/or edge extraction in the subject in the optical exposure, and having a combination unit for additive merging of the x-ray image with the extracted subject edges from the optical image associated therewith.

Described in the following are a device and a method according to the invention in which an optical video image and an associated x-ray image of a subject are acquired with identical acquisition format. The x-ray images and the video images belonging to them are brought into registration with one another and therefore respectively show the identical image section with identical scaling. This can be achieved (for example as shown in FIG. 1) by the identical video image being acquired through a semi-permeable mirror arranged in the x-ray beam cone. Through a one-time adjustment or calibration procedure, the acquisition section of the video camera is adjusted to the size of the x-ray image such that they are positioned exactly over one another. Since the subject is slightly compressed in mammography, an optically permeable upper compression plate is required. The following method steps, which can be integrated into modules, are executed to segment subjects:

(a) acquisition and storage of the individual x-ray projections,
(b) parallel to this, acquisition and storage of the associated optical video images,
(c) segmentation of the breast or subject edges in the individual video images,
(d) transfer of the segment regions or segmented edges of a subject into the x-ray images, and
(e) additional processing of the x-ray images.

The invention also has the advantage that a segmentation in the optical images can be conducted quickly, precisely and reproducibly.

The invention has the additional advantage that the subject edges in the x-ray images can be exactly specified with simultaneous dose reduction.

The invention has the further advantage that a simple algorithm for subject edge detection can be applied to the acquired high-contrast optical image.

BRIEF DESCRIPTION OF THE DRAWINGS

FIG. 1 is a schematic block diagram of an embodiment of an arrangement for imaging the subject in accordance with the invention.

FIG. 2 is a flowchart of the basic steps of an embodiment of the inventive method.

DESCRIPTION OF THE PREFERRED EMBODIMENTS

Components of a mammography apparatus are depicted in FIG. 1. With an x-ray-emitting x-ray source 1, the subject 6 positioned on a detector unit 5 is irradiated for diagnosis. A deflection unit 3 (for example a semi-permeable mirror) is arranged in the x-ray beam cone, in immediate proximity to the diaphragm aperture of the x-ray source 1, such that the individual image or individual image series acquired by a video camera 4 or a fixed frame camera corresponds exactly to the x-ray beam cone 7 emitted from the x-ray source 1. The x-ray acquisition and the optical acquisition are respectively congruent during the acquisitions of an acquisition cycle. During an acquisition or an acquisition series, the subject 6 is fixed with a compression plate on a temporary shelf or to the detector unit 5. The compression plate is fashioned to be optically transparent. The digital x-ray images cached in the detector unit 5 are stored in the memory unit SR for x-ray images. The individual images or image series acquired by the video camera 4 or the fixed frame camera are stored in a memory unit SOB for optical images. An association unit ZE associates the respective, simultaneously created individual optical images and x-ray images. The individual optical images can be present as color values or greyscale data.

A subject extraction unit VEOB downstream from the association unit ZE extracts the respective subject 6 imaged in the individual image. An extraction of the subject can ensue with a threshold or edge detection algorithm, for example. The subject edges are detected using an adaptive threshold regulation, and the data from these subject edges are stored in an additional individual image associated with the optical image. In a further processing procedure, an x-ray image associated with the respective optical image is read out from the memory unit SR for x-ray images and cached in a combination unit KE. In the combination unit KE, the respective x-ray image is loaded with the data of the subject edges. An x-ray image supplemented with subject edges is output individually or additively as a sum image to a visualization unit VE.

The processing steps in a block diagram are summarized in FIG. 2. The processing procedures specified in the preceding are summarized in three main steps in the block diagram. The respective result of the processing procedures is reflected in the x-ray images RB and optical images OB shown in FIG. 1. In the first module 11, the x-ray images RB and video images OB are acquired with the means described above, which can be aligned on one another. The image data of registered x-ray (RB) and optical (OB) image data are present at the output of the first module. As shown in FIG. 1, the image data are marked with A in the presented image data field. A segmentation of the subject 6 is produced in the second module 12. The processed image data, in particular those of the optical image OB, are present at the output of the second module 12 in the processing state shown in the image data block B. A transfer of the segmentation or subject edge and the marking of the subject boundaries into the x-ray image occurs in the third module 13. The processing result is again present at the output of a combination unit (labeled with KE). The result is reflected in the image data block C. The image data can be depicted in the visualization unit VE in combination or individual, or additively with additional representations.

Although modifications and changes may be suggested by those skilled in the art, it is the intention of the inventors to embody within the patent warranted hereon all changes and modifications as reasonably and properly come within the scope of their contribution to the art.

We claim:

1. A device for processing and presenting x-ray images, comprising:
    an x-ray acquisition unit that emits x-rays in an x-ray acquisition cone;
    an optical acquisition unit that emits light in an optical acquisition cone;
    said x-ray acquisition unit and said optical acquisition unit being oriented so that said x-ray acquisition cone and said optical acquisition cone are congruent;
    a trigger unit that activates said x-ray acquisition unit and said optical acquisition unit to simultaneously respectively acquire an x-ray image of an examination subject in said x-ray acquisition cone and an optical exposure of the same examination subject in said optical acquisition cone, said x-ray image and said optical exposure being congruent due to said x-ray acquisition and said optical acquisition cone being congruent;
    a subject extraction unit supplied with said optical exposure configured to perform an extraction procedure that identifies and extracts only a line representing an edge of the subject in said optical exposure by image segmentation, to produce an extracted edge line; and
    a computerized combination unit configured to additively combine said x-ray image and said extracted edge line with said edge line superimposed on an edge in said x-ray image corresponding to said edge in said optical exposure due to the congruency of the x-ray image and the optical exposure, to produce a combined image as an output thereof with said extracted edge line inserted into said x-ray image.

2. A device as claimed in claim 1 comprising an associated unit in which the congruent and simultaneously acquired x-ray image and optical image are associated with each other and cached.

3. A device as claimed in claim 1 wherein said x-ray unit is a digital mammography x-ray acquisition unit that produces said x-ray image by tomosynthesis with an x-ray dose that makes said edge in said x-ray image indistinct.

4. A method for processing and presenting x-ray images, comprising the steps of:
    simultaneously acquiring an x-ray image of an examination subject with an x-ray acquisition cone and an optical exposure of the examination subject with an optical acquisition cone, with said x-ray acquisition cone and said optical acquisition cone being congruent, said x-ray image and said optical exposure being congruent due to said x-ray acquisition and said optical acquisition cone being congruent;
    performing a computerized extraction procedure of the examination subject in the optical exposure that identifies and extracts only a line representing an edge of the subject in the optical exposure by image segmentation, to produce an extracted edge line; and
    in a computerized processor, additively combining said x-ray image and said extracted edge line with said edge line superimposed on an edge in said x-ray image corresponding to said edge in said optical exposure due to the congruency of the x-ray image and the optical exposure to insert said edge of said subject in said optical exposure into said x-ray image.

5. A method as claimed in claim 4 comprising storing the simultaneously acquired and congruent optical image and x-ray image in a memory.

6. A device as claimed in claim 4 comprising generating said x-ray image by tomosynthesis comprising generating a plurality of x-ray images with an x-ray dose that makes said edge in said x-ray image indistinct.

* * * * *